US00PP16745P3

(12) United States Plant Patent

Miyazaki et al.

(10) Patent No.: US PP16,745 P3
(45) Date of Patent: Jul. 4, 2006

(54) *VIOLA* PLANT NAMED 'SUNVIOLALEMO'

(50) Latin Name: *Viola cornuta*
Varietal Denomination: Sunviolalemo

(75) Inventors: Kiyoshi Miyazaki, Shiga (JP); Naoto Takamura, Shiga (JP); Yukihiro Ikeda, Hyogo (JP)

(73) Assignee: Suntory Flowers Limited, Tokyo (JP)

( * ) Notice: Subject to any disclaimer, the term of this patent is extended or adjusted under 35 U.S.C. 154(b) by 118 days.

(21) Appl. No.: 10/949,333

(22) Filed: Sep. 27, 2004

(65) Prior Publication Data

US 2006/0070154 P1 Mar. 30, 2006

(51) Int. Cl.
*A01H 5/00* (2006.01)

(52) U.S. Cl. ..... Plt./323
(58) Field of Classification Search ..... Plt./323
See application file for complete search history.

(56) References Cited

PUBLICATIONS

"Flower & Green, Autumn and Winter Catalog 2003", Published by Suntory Flowers Limited of Tokyo, Japan, Jun. 1, 2003.
"Catalog for Commercial Breeders, Autumn '97 to Spring of '98", Published by Sakata Seed Co. of Japan, 1997.
"Catalog for Commercial Producers 1997–1998", Published by Takii Seed Co. of Japan, 1997.

*Primary Examiner*—Anne Marie Grunberg
*Assistant Examiner*—June Hwu
(74) *Attorney, Agent, or Firm*—Buchanan Ingersoll PC

(57) ABSTRACT

Disclosed herein is a new and distinct variety of *Viola cornuta*, named 'Sunviolalemo'. This new variety has a spreading growth habit with long prostrate stems. This *Viola* plant has many branches, and a great profusion of blooms with the entire plant remaining in bloom for a considerable period of time. The plant displays dense green foliage, forms single medium-sized yellow flowers with some gradation of color intensity and some purple striping that are borne on the long peduncles. The flower has faint and sweet scent. The plant exhibits good resistance to rain, cold, disease and pests.

2 Drawing Sheets

Botanical classification/commercial classification: *Viola cornuta/Viola* Plant.
Varietal denomination: cv. Sunviolalemo.

BACKGROUND OF THE INVENTION

The present invention relates to a new and distinct variety of *Viola cornuta* named 'Sunviolalemo' that originated from the crossing *Viola* hybrid variety named '9V-29a' as the female parent and a variety named 'Violetto Nive' as the male parent.

In April 2000, crossing of '9V-29a' as the female parent and 'Violetto Nive' as the pollen parent was conducted at Yokaich-shi, Shiga, Japan. In May 2000, some seeds were obtained. In August 2000, the seeds from the cross were sown and 20 seedling were obtained. Three of the seedlings were selected in view of their spreading growth habit, medium flower size and yellow petal color. Those seedlings were propagated by the use of cuttings and were grown in pots, and then a plant trial was carried out beginning in October 2001, at Yokaichi-shi, Shiga, Japan. The botanical characteristics of the plant were then examined, using a parent variety, 'Violetto Nive' and a similar variety, 'Alpine Summer', for comparison. As a result, one seedling was selected and it was concluded that this *Viola* plant is distinguishable from any other variety, whose existence is known to us, and is uniform and stable in its characteristics. The new variety of *Viola* plant was named 'Sunviolalemo'.

The female parent '9V-29a' (not patented in the U.S.) is a strain from our breeding lines grown at Yokaichi-shi, Shiga, Japan, having a spreading growth habit with prostrate stems. It has larger-sized flowers than the new variety 'Sunviolalemo', and the petals are white in coloration.

The pollen parent 'Violetto Nive' is a commercial cultivar. 'Violetto Nive' (not patented in the U.S.) has a spreading growth habit with prostrate stems. It has smaller-sized flowers than the new variety 'Sunviolalemo', and the petals are white in coloration.

In the following description, the color information is in accordance with The R.H.S. Colour Chart of The Royal Horticultural Society, London, England.

SUMMARY OF THE INVENTION

This new variety is unlike any *Viola cornuta* plant that is commercially available as evidenced by the following unique combinations of characteristics.

1. Spreading growth habit having long prostrate stems and many branches.
2. A great profusion of blooms with the entire plant remaining in bloom for a considerable period of time.
3. Single, medium-sized yellow flowers having some gradation of color intensity that are borne on long peduncles.

The new variety 'Sunviolalemo' differs from the similar variety 'Violetto Nive' (not patented in the U.S.) in the following respects.

1. The stem length of 'Sunviolalemo' is longer than that of 'Violetto Nive'.
2. 'Sunviolalemo' has long-oblong leaves. Those of 'Violetto Nive' are lanceolate.

3. The peduncle length of 'Sunviolalemo' is longer than that of 'Violetto Nive'.
4. The flower of 'Sunviolalemo' is larger than that of 'Violetto Nive'.
5. The flowers of 'Sunviolalemo' and 'Violetto Nive' differ in petal color. 'Sunviolalemo' has yellow flowers with some gradation of color intensity. Those of 'Violetto Nive' are White.
6. The flowering time of 'Sunviolalemo' is earlier than that of 'Violetto Nive'.

The new variety 'Sunviolalemo' differs from the similar variety 'Alpine Summer' (not patented in the U.S.) in the following respects.

1. The stem length of 'Sunviolalemo' is longer than that of 'Alpine Summer'.
2. 'Sunviolalemo' has long-oblong leaves. Those of 'Alpine Summer' are lanceolate.
3. The peduncle length of 'Sunviolalemo' is longer than that of 'Alpine Summer'.
4. The flowers of 'Sunviolalemo' are larger than those of 'Alpine Summer'.
5. The flowers of 'Sunviolalemo' and 'Alpine Summer' differ in petal color. 'Sunviolalemo' has yellow flowers with some gradation of color intensity. Those of 'Alpine Summer' are bi-colored, the upper petal is violet, lateral and lower petals are yellow with dark purple vein.
6. Flowering time of 'Sunviolalemo' is earlier than that of 'Alpine Summer'.

The new variety of *Viola* plant 'Sunviolalemo' was asexually reproduced by the use of cuttings at Yokaichi-shi, Shiga, Japan, and the homogeneity and stability thereof were confirmed.

The instant plant retains its distinctive characteristics and reproduces true to type in successive generations.

BRIEF DESCRIPTION OF THE PHOTOGRAPHS

The accompanying photographs show, as nearly true as it is reasonably possible to make the same in color illustrations of this character, typically specimens of the new cultivar. The plants had been reproduced by the use of cuttings and were photographed during May 2002 while growing outdoors in 24 cm pots at an age of approximately 7 months at Yokaichi-shi, Shiga, Japan.

DESCRIPTION OF THE NEW VARIETY

The botanical characteristics of the new and distinct variety of *Viola cornuta* named 'Sunviolalemo' are set forth hereafter. The plants were observed during May 2002 at Yokaichi-shi, Shiga, Japan, at an age of approximately 7 months.

Plant:

*Stemmed or stemless.*—Stemmed.
*Growth habit.*—Spreading.
*Height.*—Approximately 13 cm.
*Spreading area.*—Approximately 50 cm.

Stem:

*Length.*—Approximately 48 cm.
*Color.*—R.H.S. 144B (Yellow-Green group).
*Branches.*—Many.
*Pubescence.*—Present.
*Internode length.*—Approximately 1.8 cm.

Leaf:

*Phyllotaxis.*—Alternate.
*Overall shape.*—Long oblong.
*Apex shape.*—Obtuse.
*Base shape.*—Obtuse.
*Margin.*—Crenate.
*Length.*—Approximately 3.5 cm.
*Width.*—Approximately 2.0 cm.
*Color of upper surface.*—R.H.S. 137B (Green group).
*Color of under surface.*—R.H.S. 137C (Green group).
*Leaf texture.*—Matte and smooth.
*Venation.*—Reticulate venation, not apparent except towards the central venation.
*Petiole length.*—Approximately 1.7 cm.
*Petiole diameter.*—Approximately 0.8 mm.
*Petiole color.*—144D (Yellow-Green group).
*Stipule.*—Approximately 2.5 cm in length, and approximately 2.0 cm in width. Pinnately parted. Shape is narrowly ovate. Upper surface color is R.H.S.137B (Green group). Under surface color is R.H.S.137C (Green group).

Figure 1:
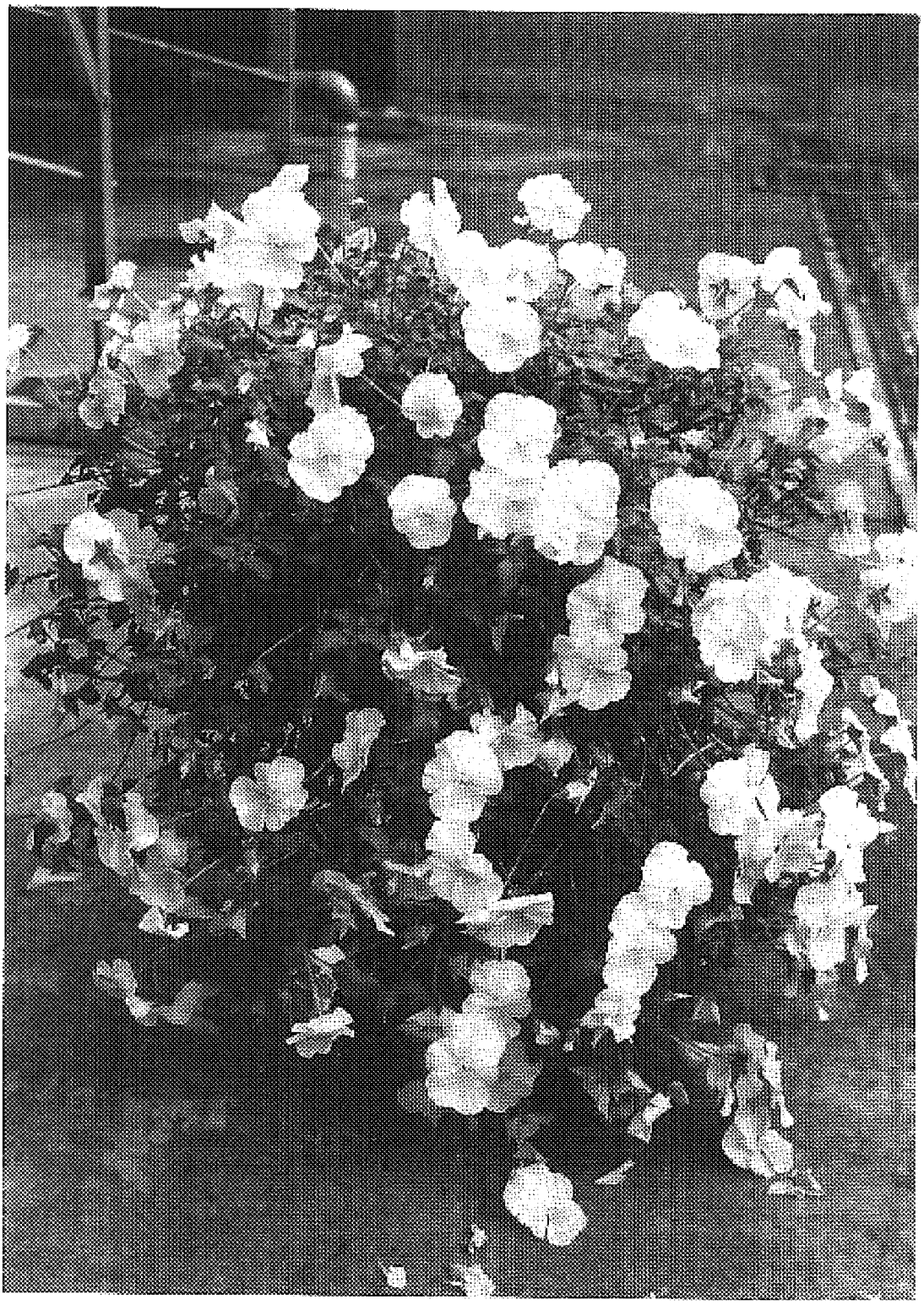
FIG. 1 illustrates an entire flowering plant of the new variety while growing in a pot.
Figure 2:
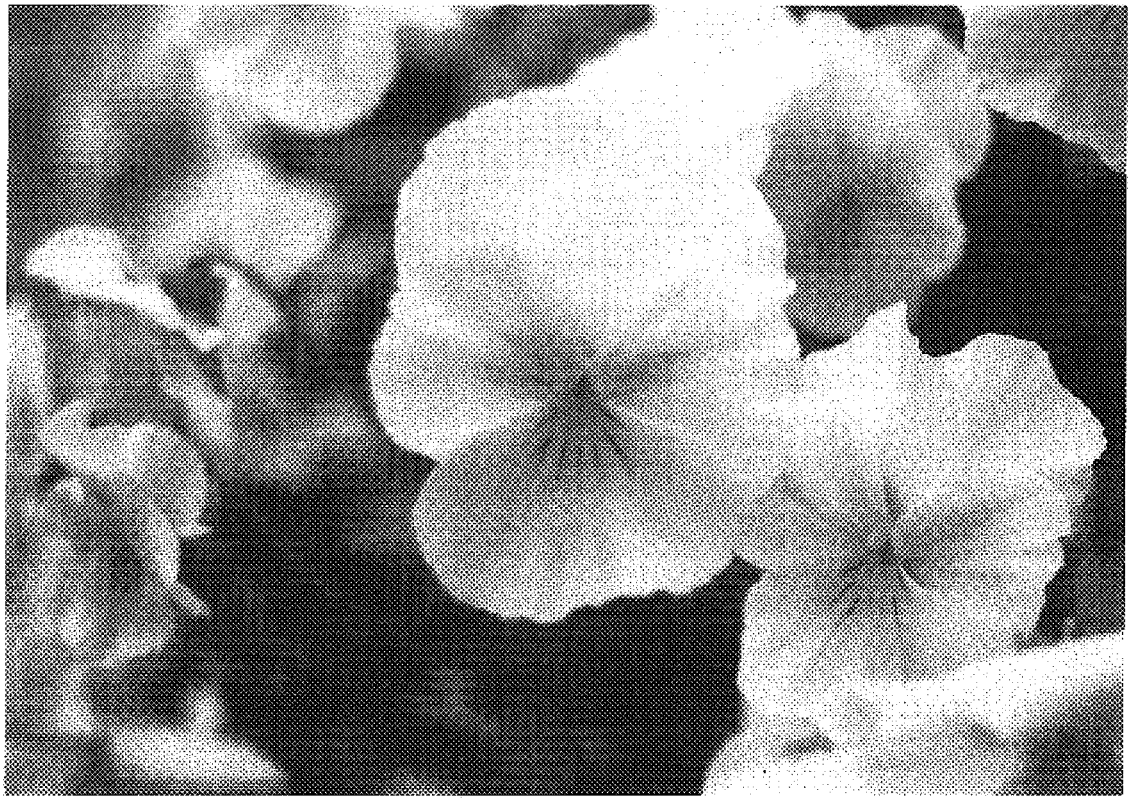
FIG. 2 illustrates a close view of the blossoms of the new variety.

Flower:

*Inflorescence.*—Flower solitary, axillary.
*Flower form.*—Single, having 5 petals, i.e., 2 upper petals, 2 lateral petals, and a spurred lower petal.
*Longitudinal diameter.*—Approximately 5.5 cm.
*Horizontal diameter.*—Approximately 4.5 cm.
*Flower depth.*—Approximately 0.9 cm.
*Petal margin.*—Entire, flat.
*Flower color.*—Primarily yellow with some gradation of the color intensity. Upper petal: R.H.S.9D (Yellow group). Lateral petal: R.H.S.6D (Yellow group), and near the throat there are stripes of N79A (Purple group) as illustrated in FIG. 2, and near the throat the coloration commonly approaches R.H.S. 9D (Yellow group) and is accompanied by some pubescence. Lower petal: R.H.S.9B (Yellow group), and near the throat there are stripes of N79A (Purple group) as illustrated in FIG. 2.
*Petal size.*—(Length×width). Upper petal: Approximately 3.5 cm×3.2 cm. Lateral petal: Approximately 2.0 cm×1.5 cm. Lower petal: Appoximately 2.3 cm×3.4 cm.
*Petal shape.*—Upper petal: Rounded. Lateral petal: Ovate. Lower petal: Cordate, spurred.
*Eye color.*—R.H.S.14A (Yellow-Orange group) on the lower petal.
*Eye size.*—Length: Approximately 5.0 mm. Width: Approximately 4.5 mm.
*Spur length.*—Approximately 5.0 mm.
*Spur diameter.*—Approximately 1.3 mm.
*Spur color.*—R.H.S.189B (Greyed-Green group).
*Sepal.*—5 sepals, unequal, approximately 0.8 cm–1.5 cm in size, narrowly triangular, include short extensions and R.H.S. 144A (Yellow-Green group) in coloration on both surfaces.
*Number of flowers.*—November to March: Approximately 10 flowers per a plant. March to June: Approximately 40–50 flowers per a plant.
*Peduncle length.*—Approximately 12 cm.
*Peduncle thickness.*—Approximately 1.3 mm.
*Peduncle color.*—R.H.S.137D (Green group).

Reproductive organs:

*Stamen.*—Five stamens joined around the ovary. Two lower stamens commonly are spurred.
*Stamen length.*—Approximately 3.0 mm.

*Anther color.*—R.H.S.9D (Yellow group). Tip: R.H.S. 166B (Greyed-Orange group).
*Pollen color.*—R.H.S.9D (Yellow group).
*Pistil length.*—Approximately 6.0 mm.
*Stigma shape.*—Ellipsoidal.
*Stimga length.*—Approximately 1.5 mm.
*Stigma color.*—R.H.S. 154B (Yellow-Green group).
*Style length.*—Approximately 1.0 mm.
*Style color.*—R.H.S. 154C (Yellow-Green group).
*Ovary color.*—R.H.S. 149D (Yellow-Green group).

Seeds:

*Seeds.*—Some seed development has been observed.
*Seeds color.*—R.H.S. 165A (Greyed-Orange group).
*Size* .—Approximately 2.0 mm in length, and approximately 1.0 mm in width.

Physical characteristics:

*Blooming period.*—Early November to June in Japan, except Hokkaido. A bloom commonly lasts 5–7 days on the plant.
*Fragrance.*—Faint and somewhat sweet.
*Rain tolerance.*—Strong.

This variety has survived temperatures of at least as low as −7° C.

The plant grows well at temperature up to 25 ° C.

The lower and upper temperatures for the plant survival have not been evaluated in detail.

No serious damage by white flies, aphids, and fungal and bacterial diseases has been observed.

This new variety of *Viola* plant 'Sunviolalemo' is most suitable for potting, and for growing in hanging baskets and in flower beds.

It is claimed:

1. A new and distinct variety of *Viola cornuta* plant named 'Sunviolalema', substantially as herein illustrated and described.

* * * * *